US008218716B2

(12) United States Patent
Handa et al.

(10) Patent No.: US 8,218,716 B2
(45) Date of Patent: Jul. 10, 2012

(54) RADIATION TOMOGRAPHY METHOD

(75) Inventors: Takanobu Handa, Tokyo (JP); Shuji Kaneko, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 32 days.

(21) Appl. No.: 12/679,102

(22) PCT Filed: Sep. 14, 2009

(86) PCT No.: PCT/JP2009/066020
§ 371 (c)(1),
(2), (4) Date: Jul. 8, 2010

(87) PCT Pub. No.: WO2011/030460
PCT Pub. Date: Mar. 17, 2011

(65) Prior Publication Data
US 2011/0268244 A1 Nov. 3, 2011

(51) Int. Cl.
*A61B 6/00* (2006.01)
*A61N 5/10* (2006.01)
(52) U.S. Cl. .............................. 378/4; 378/65
(58) Field of Classification Search .................. 378/4, 8, 378/9, 65
See application file for complete search history.

(56) References Cited

U.S. PATENT DOCUMENTS

| | | | |
|---|---|---|---|
| 5,175,754 A | 12/1992 | Casey et al. | |
| 5,262,946 A * | 11/1993 | Heuscher | 378/15 |
| 5,606,585 A * | 2/1997 | Hu | 378/15 |
| 5,825,842 A * | 10/1998 | Taguchi | 378/15 |
| 5,828,718 A * | 10/1998 | Ruth et al. | 378/19 |
| 6,061,422 A * | 5/2000 | Miyazaki et al. | 378/15 |
| 6,466,640 B1 * | 10/2002 | Taguchi | 378/15 |
| 6,621,889 B1 * | 9/2003 | Mostafavi | 378/65 |
| 6,876,719 B2 * | 4/2005 | Ozaki | 378/7 |
| 7,551,717 B2 * | 6/2009 | Tome et al. | 378/65 |
| 8,014,489 B2 * | 9/2011 | Oshima | 378/8 |

(Continued)

FOREIGN PATENT DOCUMENTS
JP 60-207645 10/1985
(Continued)

OTHER PUBLICATIONS
Matsuda, English traslation of JP 200723677A, 2007, pp. 1-16.*
(Continued)

*Primary Examiner* — Alexander H Taningco
(74) *Attorney, Agent, or Firm* — Wenderoth, Lind & Ponack, L.L.P.

(57) ABSTRACT

A radiation tomography method of the present invention includes: calculating a radiating timing, with reference to imaging timing correction data relating a plurality of gantry angles to a plurality of imaging timing correction amounts, on the basis of an imaging timing at which a radiation source supported by a rotating traveling gantry is arranged at a predetermined imaging angle and an imaging timing correction amount, of the plurality of imaging timing correction amounts, related to a gantry angle at which the traveling gantry is arranged at the imaging timing; and calculating, on the basis of an X-ray image imaged with a radiation radiated from the radiation source at the radiating timing, three-dimensional data of the X-ray image of a subject. According to the radiation tomography method, the X-ray image imaged with the further accurately arranged radiation can be obtained even in a case where the traveling gantry deflects depending on the gantry angle at which the traveling gantry is arranged, and thus the three-dimensional data can be obtained more accurately.

21 Claims, 7 Drawing Sheets

U.S. PATENT DOCUMENTS

2008/0095307 A1  4/2008  Ishida et al.

FOREIGN PATENT DOCUMENTS

| | | | |
|---|---|---|---|
| JP | 01059186 A | * | 3/1989 |
| JP | 6-22952 | | 2/1994 |
| JP | 8-24251 | | 1/1996 |
| JP | 2002172112 A | * | 6/2002 |
| JP | 2004-065287 | | 3/2004 |
| JP | 2005-177260 | | 7/2005 |
| JP | 2006-180910 | | 7/2006 |
| JP | 2007-236777 | | 9/2007 |
| JP | 2007236777 A | * | 9/2007 |
| JP | 2008-132313 | | 6/2008 |

OTHER PUBLICATIONS

International Search Report issued Nov. 2, 2009 in International (PCT) Application No. PCT/JP2009/066020 (English language translation provided).

* cited by examiner

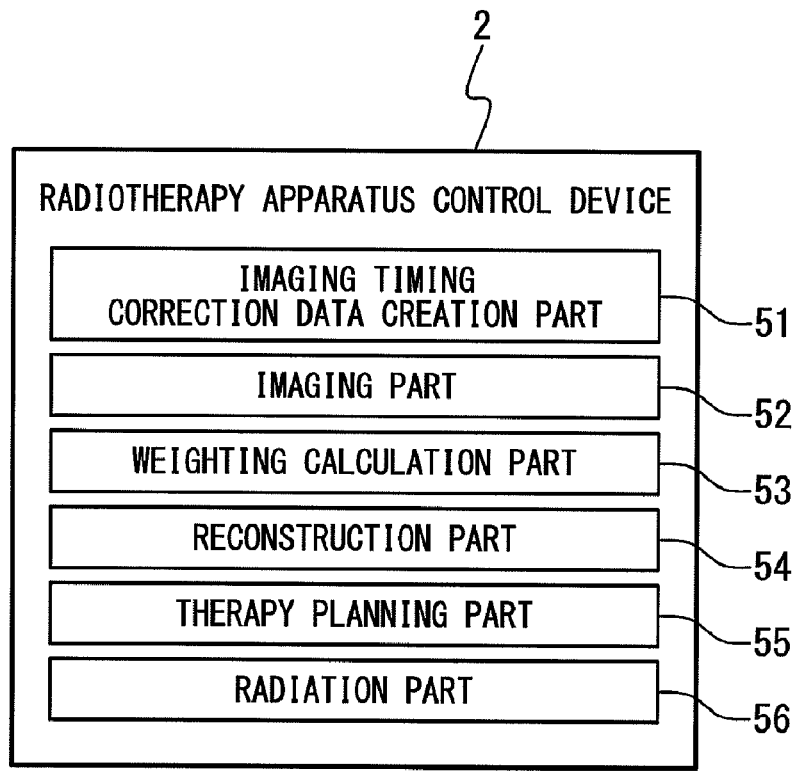

RADIATION TOMOGRAPHY METHOD

TECHNICAL FIELD

The present invention relates to a radiation tomography method, and especially relates to a radiation tomography method used for reconstructing transmission images of a subject into three-dimensional data of the subject.

BACKGROUND ART

A computer tomography device is known, which processes transmission images of a subject taken from the respective directions and reconstructs three-dimensional CT data of the subject. In a case where a human body is the subject, this computer tomography device requires the subject human to stop his/her breath during the imaging in order to obtain a highly-accurate image free from jiggle caused by the respiratory displacement. To reduce a burden of a patient, it is required to shorten an imaging period of the X-ray image. A cone beam CT (CBCT: Cone Beam Computed Tomography) is known, which reconstructs the three-dimensional CT data of the subject on the basis of a plurality of X-ray images imaged by using a conically-shaped (cone-shaped) X-ray radiated from a radiation source rotating around the subject to the subject. This cone beam CT can create the three-dimensional CT data in a short time without rotating the radiation source more than once. Moreover, this cone beam CT is required to calculate the three-dimensional data more accurately.

Japanese Patent Publication JP 2005-177260 A discloses an X-ray computer tomography device for reducing influence of scattered radiations in a multi-tube type X-ray computer tomography device. The X-ray computer tomography device is characterized by including: a plurality of X-ray tubes; a plurality of X-ray detectors corresponding to the plurality of X-ray tubes respectively; a plurality of high voltage generation parts corresponding to the plurality of X-ray tubes respectively; a plurality of data collection parts corresponding to the plurality of X-ray tubes respectively; a substantially-circular frame provided to be rotatable for mounting the plurality of X-ray tubes, the plurality of X-ray detectors, the plurality of high voltage generation parts, and the plurality of data collection parts; and a control part for controlling the plurality of high voltage generation parts so that a pulse X-ray can be generated shifting in each $\tau/n$ ($\tau$: a pulse duration time and n: a positive real number) in the order from the plurality of X-ray tubes.

Japanese Patent Publication JP 2007-236777 A discloses an X-ray CT device able to obtain an image where influence of the artifact is suppressed. In the X-ray CT device, a plurality of pairs of an X-ray tube and an X-ray detector are arranged at different angles and the pairs are configured to be rotatable, and the X-ray CT device includes: a control part for controlling a timing of the X-ray detection by the X-ray detectors; and a reconstruction processing part for generating image data by carrying out a reconstruction process to outputs of the X-ray detectors, wherein the control part makes the respective X-ray detectors detect X-rays at different timings on the basis of relative positions of the pairs composed of the X-ray tube and the X-ray detector.

CITATION LIST

Patent Literature
Patent literature 1: JP 2005-177260 A
Patent literature 2: JP 2007-236777 A

SUMMARY OF INVENTION

A purpose of the present invention is to provide a radiation tomography method for calculating more accurately three-dimensional data reconstructed on the basis of a plurality of X-ray images.

A radiation tomography method of the present invention includes: calculating a radiating timing, with reference to imaging timing correction data relating a plurality of gantry angles to a plurality of imaging timing correction amounts, on the basis of an imaging timing at which a radiation source supported by a rotating traveling gantry is arranged at a predetermined imaging angle and an imaging timing correction amount, of the plurality of imaging timing correction amounts, related to a gantry angle at which the traveling gantry is arranged at the imaging timing; and calculating, on the basis of an X-ray image imaged with a radiation radiated from the radiation source at the radiating timing, three-dimensional data of the X-ray image of a subject. According to the radiation tomography method, the X-ray image imaged with the further accurately arranged radiation can be obtained even in a case where the traveling gantry deflects depending on the gantry angle at which the traveling gantry is arranged, and thus the three-dimensional data can be obtained more accurately.

The radiation tomography method of the present invention further includes: calculating another radiating timing. The imaging timing correction data further relates the plurality of gantry angles to a plurality of other imaging timing correction amounts. The other radiating timing is calculated on the basis of: another imaging timing at which another radiation source supported by the traveling gantry is arranged at another predetermined imaging angle; and another imaging timing correction amount, of the plurality of other imaging timing correction amounts, related to another gantry angle at which the traveling gantry is arranged at the other imaging timing. The three-dimensional data is calculated further on the basis of another X-ray image imaged with another radiation radiated at the other radiating timing from the other radiation source. According to this radiation tomography method, the three-dimensional data further can be calculated more accurately even in a case where the X-ray images are imaged with two radiations radiated from the two radiation sources.

The other radiation is radiated in a period where the radiation is not radiated. The radiation is radiated in a period where the other radiation is not radiated. On this occasion, in the X-ray image imaged with the radiation, influence of scattered radiations caused by the other radiation is reduced, and in the X-ray image imaged with the other radiation, influence of scattered radiations caused by the radiation is reduced. As the result, according to this radiation tomography method, the three-dimensional data can be calculated more accurately.

The predetermined imaging angle and the other imaging angle are formed so as to coincide to anyone of the plurality of imaging angles having equal intervals. According to this radiation tomography method, the three-dimensional data can be calculated more accurately.

It is preferable that the radiation tomography method of the present invention further includes: measuring a plurality of first absolute angles at which the radiation source is arranged when the traveling gantry is arranged at the plurality of gantry angles; measuring a plurality of second absolute angles at which the other radiation source is arranged when the traveling gantry is arranged at the plurality of gantry angles; and creating the imaging timing correction data on the basis of the plurality of first absolute angles and the plurality of second absolute angles.

The radiation tomography method of the present invention further includes: calculating a plurality of weightings related to a plurality of X-ray images to be reconstructed to the three-dimensional data on the basis of the X-ray image and the predetermined image angle. The plurality of X-ray images is related to the plurality of imaging angles. The plurality of weightings is calculated so that, when in-unit-angle X-ray images of the plurality of X-ray images are related to in-unit-angle imaging angles included in a unit angle range, a summation of in-unit-angle weightings related to the in-unit-angle X-ray images, of the plurality of weightings, can be even. The three-dimensional data is further calculated on the basis of the plurality of weightings. According to this radiation tomography method, the three-dimensional data can be calculated more accurately even in a case where the plurality of imaging angles related to the plurality of X-ray images are not in equal intervals.

A computer readable recording medium of the present invention, records a computer program causing the computer to execute the radiation tomography method of the present invention.

A radiotherapy apparatus control device of the present invention includes: an imaging part imaging an X-ray image, with reference to imaging timing correction data relating a plurality of gantry angle to a plurality of imaging timing correction amounts, by radiating a radiation from a radiation source at a radiating timing calculated on the basis of an imaging timing at which the radiation source supported by a rotating traveling gantry is arranged at a predetermined imaging angle and an imaging timing correction amount, of the plurality of imaging timing correction amounts, related to a gantry angle at which the traveling gantry is arranged at the imaging timing; and a reconstruction part calculating three-dimensional data of the X-ray image of a subject on the basis of the X-ray image. According to the radiotherapy apparatus control device, an X-ray image imaged with the further accurately arranged radiation can be obtained even in a case where the traveling gantry deflects depending on the gantry angle at which the traveling gantry is arranged, and thus the three-dimensional data can be obtained more accurately.

The imaging timing correction data further relates the plurality of gantry angles to a plurality of other imaging timing correction amounts. The imaging part calculates another radiating timing on the basis of: another imaging timing at which another radiation source supported by the traveling gantry is arranged at another predetermined imaging angle; and another imaging timing correction amount, of the plurality of other imaging timing correction amounts, related to another gantry angle at which the traveling gantry is arranged at the other imaging timing, and images another X-ray image by radiating another radiation radiated at the other radiating timing from the other radiation source. On this occasion, the reconstruction part calculates the three-dimensional data further on the basis of the other X-ray image. According to this radiotherapy apparatus control device, the three-dimensional data further can be calculated more accurately even in a case where the x-ray images are imaged with two radiations radiated from the two radiation sources.

The other radiation is radiated in a period where the radiation is not radiated. The radiation is radiated in a period where the other radiation is not radiated. On this occasion, in the X-ray image imaged by the radiation, influence of scattered radiations caused by the other radiation is reduced, and in the X-ray image imaged by the other radiation, influence of scattered radiations caused by the radiation is reduced. As the result, according to this radiotherapy apparatus control device, the three-dimensional data can be calculated more accurately.

The predetermined imaging angle and the other imaging angle are formed so as to coincide to anyone of the plurality of imaging angles having equal intervals. On this occasion, the three-dimensional data can be calculated more accurately.

It is preferable that the radiotherapy apparatus control device further includes an imaging timing correction data creation part creating the imaging timing correction data on the basis of a plurality of first absolute angles of the radiation source measured when the traveling gantry is arranged at the plurality of gantry angles and a plurality of second absolute angles of the other radiation source measured when the traveling gantry is arranged at the plurality of gantry angles.

The radiotherapy apparatus control device of the present invention further includes a weighting calculation part calculating a plurality of weightings related to the plurality of X-ray images to be reconstructed to the three-dimensional data on the basis of the X-ray image and the predetermined image angle. The plurality of X-ray images is related to the plurality of imaging angles. The plurality of weightings is calculated so that, when in-unit-angle X-ray images of the plurality of X-ray images are related to in-unit-angle imaging angles included in a unit angle range, a summation of in-unit-angle weightings related to the in-unit-angle X-ray images, of the plurality of weightings, can be even. The reconstruction part calculates the three-dimensional data further on the basis of the plurality of weightings. According to this radiotherapy apparatus control device, the three-dimensional data can be calculated more accurately even in a case where the plurality of imaging angles related to the plurality of X-ray images are not in equal intervals.

A radiotherapy system of the present invention includes the radiotherapy apparatus and the radiotherapy apparatus control device according to the present invention. It is preferable that the radiotherapy apparatus includes the radiation source and the traveling gantry.

It is preferable that the radiotherapy apparatus further includes a therapeutic radiation radiating device for radiating therapeutic radiation. The therapeutic radiation radiating device is fixed to the traveling gantry.

According to the radiation tomography method of the present invention, X-ray images can be imaged with radiations arranged more accurately, and as the result, three-dimensional data of a subject can be calculated with high accuracy.

BRIEF DESCRIPTION OF DRAWINGS

FIG. 3 is a block diagram showing a radiotherapy apparatus control device;

FIG. 4 is a diagram showing imaging timing correction data;

DESCRIPTION OF EMBODIMENTS

Figure 1:
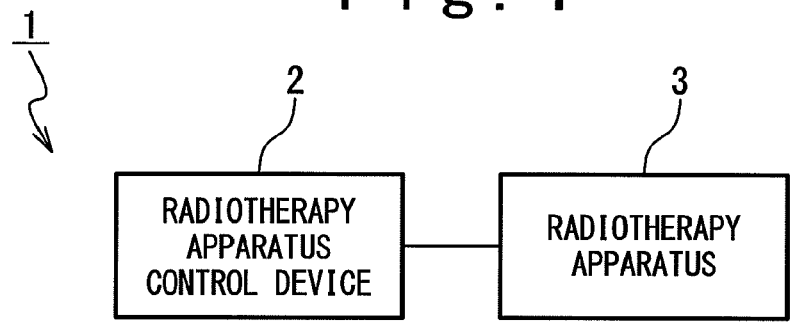
FIG. 1 is a block diagram showing an embodiment of a radiotherapy system according to the present invention.

Referring to drawings, an embodiment of a radiotherapy system according to the present invention will be described. As shown in FIG. 1, a radiotherapy system 1 includes a radiotherapy apparatus control device 2 and a radiotherapy apparatus 3. The radiotherapy apparatus control device 2 is a computer exemplified by a personal computer. The radiotherapy apparatus control device 2 and the radiotherapy apparatus 3 are connected with each other so as to execute two-way communication.

Figure 2:
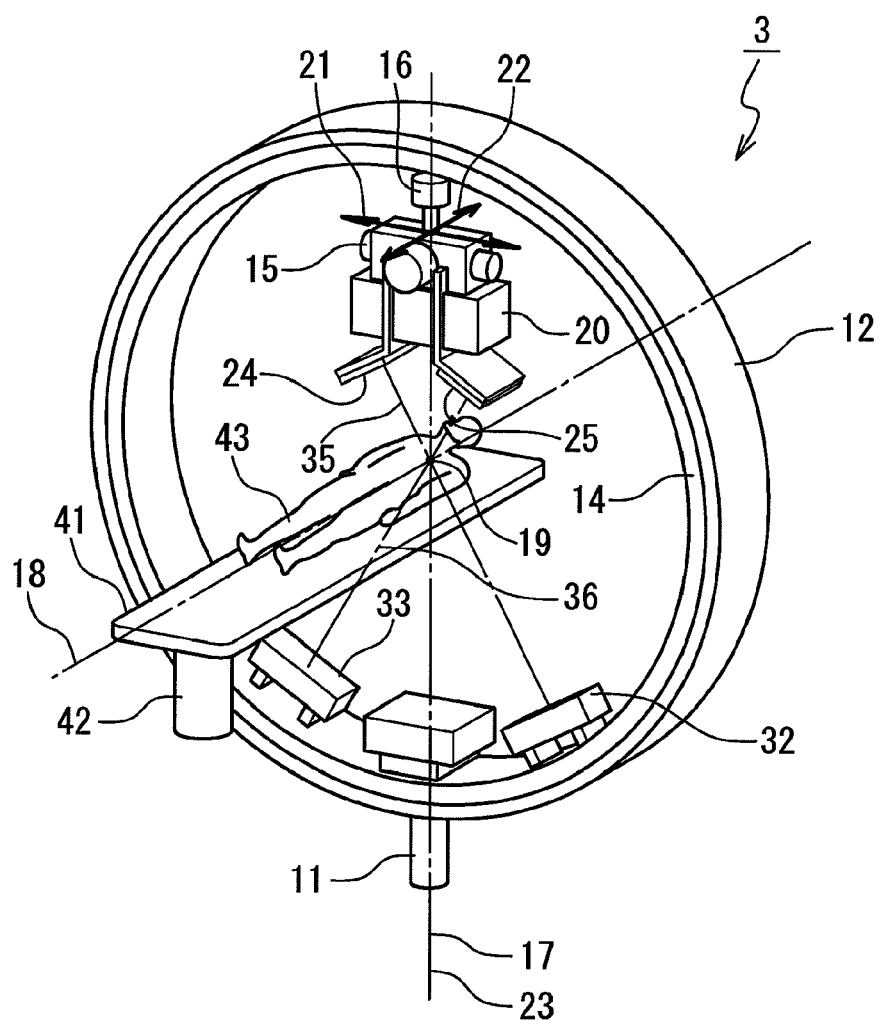
FIG. 2 is a perspective view showing a radiotherapy apparatus.

FIG. 2 shows the radiotherapy apparatus 3. The radiotherapy apparatus 3 includes an O-ring 12, a travelling gantry 14, and a therapeutic radiation radiating device 16. The O-ring 12 is formed to be a ring-shape, and is supported on a base so as to be rotatable around a rotational axis 17. The rotational axis 17 is parallel to a vertical direction. The travelling gantry 14 is formed to be a ring-shape, is arranged inside a ring of the O-ring 12, and is supported by the O-ring 12 so as to be rotatable around the rotation axis 18. The rotation axis 18 is perpendicular to the vertical direction, and passes through an isocenter 19 included in the rotation axis 17. The rotation axis 18 is secured to the O-ring 12, namely, rotates around the rotation axis 17 together with the O-ring 12.

The therapeutic radiation radiating device 16 is arranged inside the ring of the traveling gantry 14. The therapeutic radiation radiating device 16 is supported by the traveling gantry 14 so as to be rotatable around a tilt axis 21 and to be rotatable around a pan axis 22. The pan axis 22 is secured to the traveling gantry 14, and is parallel to the rotation axis 18 without intersecting with the rotation axis 18. The tilt axis 21 is at right angles to the pan axis 22. An intersection point of the two axes, the tilt axis 21 and the pan axis 22, is separated one meter away from the isocenter 19.

The radiotherapy apparatus 3 further includes a turn drive device 11 and a head swing mechanism 15, and includes a traveling drive device not shown in the drawings. The turn drive device 11 rotates the O-ring 12 around the rotation axis 17 when controlled by the radiotherapy apparatus control device 2. The traveling drive device rotates the traveling gantry 14 around the rotation axis 18 when controlled by the radiotherapy apparatus control device 2. The traveling drive device further measures a gantry angle to the O-ring 12 at which the traveling gantry 14 is arranged, and outputs the gantry angle to the radiotherapy apparatus control device 2. The head swing mechanism 15 rotates the therapeutic radiation radiating device 16 around the pan axis 22 and rotates the therapeutic radiation radiating device 16 around the tilt axis 21 when controlled by the radiotherapy apparatus control device 2.

The therapeutic radiation radiating device 16 radiates therapeutic radiation 23 when controlled by the radiotherapy apparatus control device 2. The therapeutic radiation 23 is a cone beam having an apex that is an intersection point where the pan axis 22 and the tilt axis 21 intersect with each other. The therapeutic radiation 23 is formed so as to have a uniform intensity distribution. The therapeutic radiation radiating device 16 includes a multi-leaf collimator 20. The multi-leaf collimator 20 is secured to the therapeutic radiation radiating device 16 so as to be arranged in a region where the therapeutic radiation 23 travels. The multi-leaf collimator 20 shields a part of the therapeutic radiation 23 to change a shape of an irradiation field in which the therapeutic radiation 23 is radiated to a patient when controlled by the radiotherapy apparatus control device 2.

When the therapeutic radiation radiating device 16 is supported by the traveling gantry 14 in this manner and thereby therapeutic radiation radiating device 16 is secured to the traveling gantry 14 so as to face the isocenter 19, the therapeutic radiation 23 constantly passes almost through the isocenter 19 even when the O-ring is rotated by the turn drive device 11 or the traveling gantry 14 is rotated by the traveling drive device. That is, the therapeutic radiation 23 can be radiated from an arbitrary direction toward the isocenter 19 by carrying out the travelling and turning.

The radiotherapy apparatus 3 further includes a plurality of imager systems. Specifically, the radiotherapy apparatus 3 includes a first diagnostic X-ray source 24, a second diagnostic X-ray source 25, a first sensor array 32, and a second sensor array 33. The first diagnostic X-ray source 24 is supported by the traveling gantry 14, and is arranged inside the ring of the traveling gantry 14 so that an angle defined by a line segment connecting between the isocenter 19 and the first diagnostic X-ray source 24 and a line segment connecting between the isocenter 19 and the therapeutic radiation radiating device 16 can be an acute angle. The second diagnostic X-ray source 25 is supported by the traveling gantry 14, and is arranged inside the ring of the traveling gantry 14 so that an angle defined by a line segment connecting between the isocenter 19 and the second diagnostic X-ray source 25 and a line segment connecting between the isocenter 19 and the therapeutic radiation radiating device 16 can be an acute angle. Further, the second diagnostic X-ray source 25 is arranged so that an angle defined by a line segment connecting between the isocenter 19 and the first diagnostic X-ray source 24 and a line segment connecting between the isocenter 19 and the second diagnostic X-ray source 25 can be a right angle (90 degree). The first sensor array 32 is supported by the traveling gantry 14, and is arranged so as to face the first diagnostic X-ray source 24 via the isocenter 19. The second sensor array 33 is supported by the traveling gantry 14, and is arranged so as to face the second diagnostic X-ray source 25 via the isocenter 19.

The first diagnostic X-ray source 24 radiates a first diagnostic X-ray 35 to the isocenter 19 at a predetermined timing, when controlled by the radiotherapy apparatus control device 2. The first diagnostic X-ray 35 is radiated from one point included in the first diagnostic X-ray source 24, and is a conically-shaped cone beam having the one point as the apex. The second diagnostic X-ray source 25 radiates a second diagnostic X-ray 36 to the isocenter 19 at a predetermined timing, when controlled by the radiotherapy apparatus control device 2. The second diagnostic X-ray 36 is radiated from one point included in the second diagnostic X-ray source 25, and is a conically-shaped cone beam having the one point as the apex.

The first sensor array 32 has a light receiving part. The light receiving part is formed so that a spread angle defined by two straight lines connecting both ends of the light receiving part along a rotation direction of the traveling gantry 14 to an apex of the first diagnostic X-ray 35 can be 12.0 degrees. The first sensor array 32 generates an X-ray image on the basis of the X-ray received by the light receiving part, when controlled by the radiotherapy apparatus control device 2. The second sensor array 33 has a light receiving part. The light receiving part is formed so that a spread angle defined by two straight lines connecting both ends of the light receiving part along the rotation direction of the traveling gantry 14 to an apex of the second diagnostic X-ray 36 can be 12.0 degrees. The second sensor array 33 generates an X-ray image on the basis of the X-ray received by the light receiving part, when controlled by the radiotherapy apparatus control device 2. Each X-ray image is formed of a plurality of pixels. The plurality of pixels is arranged in a matrix shape on the X-ray image, and each pixel is related to brightness. The X-ray image shows the subject by coloring each of the plurality of pixels using the brightness related to each of the plurality of pixels. A FPD (Flat Panel Detector) and an X-ray II (Image intensifier) are exemplified as the first sensor array 32 and the second sensor array 33.

According to this imager system, the X-ray image including the isocenter 19 as the center can be generated on the basis of image signals obtained by the first sensor array 32 and the second sensor array 33.

The radiotherapy apparatus 3 further includes a couch 41 and a couch drive device 42. The couch 41 is supported on the base so as to move parallel. The couch 41 is used for that the patient 43 to be treated by the radiotherapy system 1 lies. The couch 41 has a fixture member not shown in the drawing. The fixture member fixes the patient on the couch 41 so that the patient cannot move. The couch drive device 42 moves the couch 41 parallel when controlled by the radiotherapy apparatus control device 2.

FIG. 3 shows the radiotherapy apparatus control device 2. The radiotherapy apparatus control device 2 is a computer, and includes a CPU, a storage device, a removable memory drive, an input device, an output device, and an interface, which are not shown in the drawings. The CPU executes a computer program installed in the radiotherapy apparatus control device 2 to control the storage device, the input device, and the output device. The storage device records the computer program, records information used by the CPU, and records information generated by the CPU. The removable memory drive is used for when a recording medium is inserted, reading data recorded in the recording medium. The removable memory drive is used for especially when the recording medium that records the computer program is inserted, installing the computer program to the radiotherapy apparatus control device 2. The input device outputs the information generated by an operation of a user to the CPU. A keyboard and a mouse are exemplified as the input device. The output device outputs the information generated by the CPU to the user in a recognizable manner. A display is exemplified as the output device.

The interface outputs the information generated by an external apparatus connected to the radiotherapy apparatus control device 2 to the CPU, and outputs the information generated by the CPU to the external apparatus. The external apparatus includes the turn drive device 11 of the radiotherapy apparatus 3, the traveling drive device, the head swing mechanism 15, the therapeutic radiation radiating device 16, the multi-leaf collimator 20, the first diagnostic X-ray source 24, the second diagnostic X-ray source 25, the first sensor array 32, the second sensor array 33, and the couch drive device 42.

The computer program to be installed in the radiotherapy apparatus control device 2 is formed of a plurality of computer programs for making the radiotherapy apparatus control device 2 realize a plurality of functions. The plurality of functions includes an imaging timing correction data creation part 51, an imaging part 52, a weighting calculation part 53, a reconstruction part 54, a therapy planning part 55, and a radiation part 56.

The imaging timing correction data creation part 51 creates imaging timing correction data on the basis of deflection data inputted by using the input device, and records the imaging timing correction data to the storage device. The deflection data relates a gantry angle set to a first measurement angle set and a second measurement angle set. That is, an arbitrary element of the gantry angle set relates to one element of the first measurement angle set and to one element of the second measurement angle set. The element of the gantry angle set shows a gantry angle at which the traveling gantry 14 is arranged to the O-ring 12, and shows the gantry angle measured by the traveling drive device of the radiotherapy apparatus 3. An element, relating to a gantry angle, of the first measurement angle set shows an angle at which the first diagnostic X-ray source 24 is arranged to the O-ring 12 when the gantry angle has been measured by the traveling drive device of the radiotherapy apparatus 3. An element, relating to a gantry angle, of the second measurement angle set shows an angle at which the second diagnostic X-ray source 25 is arranged to the O-ring 12 when the gantry angle has been measured by the traveling drive device of the radiotherapy apparatus 3.

The imaging part 52 controls the radiotherapy apparatus 3 so that a plurality of X-ray images showing the patient 43 arranged on the isocenter 19 can be imaged. Namely, the imaging part 52 controls the turn drive device 11 so that the O-ring 12 can be arranged to the base at a predetermined turn angle. The imaging part 52 further controls the traveling drive device of the radiotherapy apparatus 3 so that the traveling gantry 14 can rotate around the rotation axis 18 at a constant angular velocity (for example, 7 degrees per second). The imaging part 52 further controls the first diagnostic X-ray source 24 so that while the traveling gantry 14 rotates around the rotation axis 18, the respective first diagnostic X-rays 35 can be radiated at timings when the first diagnostic X-ray source 24 is arranged to the O-ring 12 at a plurality of first imaging angles. Moreover, the imaging part 52 controls the second diagnostic X-ray source 25 so that while the traveling gantry 14 rotates around the rotation axis 18, the respective second diagnostic X-rays 36 can be radiated at timings when the second diagnostic X-ray source 25 is arranged to the O-ring 12 at a plurality of second imaging angles. The first imaging angles and the second imaging angles are designed so as to substantially correspond to a plurality of angles. The plurality of angles is obtained by dividing evenly a range (hereinafter referred to as "an imaging angle range" in the present specification) with equal intervals. The range is from the minimum value to the maximum value of a plurality of imaging angles, where the plurality of X-ray images is imaged. The imaging part 52 further controls the first sensor array 32 so that first X-ray images can be created when the traveling gantry 14 is arranged to the O-ring 12 at a plurality of gantry angles. Furthermore, the imaging part 52 controls the second sensor array 33 so that second X-ray images can be created when the traveling gantry 14 is arranged to the O-ring 12 at a plurality of gantry angles. The plurality of gantry angles is designed so as to correspond to the gantry angles at which the traveling gantry 14 is arranged when the first diagnostic X-rays 35 are arranged at the first imaging angles and so as to correspond to the gantry angles at which the traveling gantry 14 is arranged when the second diagnostic X-rays 36 are arranged at the second imaging angles.

The weighting calculation part 53 calculates a plurality of weightings on the basis of the plurality of first X-ray images and the plurality of second X-ray images imaged by the imaging part 52. The plurality of weightings corresponds to the plurality of first X-ray images and the plurality of second X-ray images. That is, an arbitrary image of the plurality of first X-ray images corresponds to one of the plurality of weightings. An arbitrary image of the plurality of second X-ray images corresponds to one of the plurality of weightings. The plurality of weightings is calculated so that a summation may be equal to a first value. The plurality of weightings is further calculated so that, when the number of the X-ray images imaged at imaging angles within an arbitrary range having a predetermined width included in the imaging angle range is n, a summation of n number of weightings corresponding to the n number of X-ray images may be equal to a second value. The second value is calculated so that a ratio between a width of a plurality of imaging angles at which a plurality of X-ray images respectively is imaged by the imaging part 52 and the arbitrary width may correspond to a ratio between the first value and the second value.

The reconstruction part 54 calculates three-dimensional data on the basis of the plurality of first X-ray images imaged by the imaging part 52, the plurality of second X-ray images imaged by the imaging part 52, and the plurality of weightings calculated by the weighting calculation part 53. The three-dimensional data shows a stereoscopic shape of an organ of the patient 43, and relates a plurality of transmittances to a plurality of voxels. The plurality of voxels corresponds to a plurality of rectangular parallelepipeds closely filled in a space where the patient 43 is arranged, respectively. A cube whose one side has a length of 0.4 mm is exemplified as the rectangular parallelepiped. The transmittance corresponding to each of the voxels shows a transmittance of the X-ray of the cube arranged on a position corresponding to each of the voxels. This reconstruction is commonly known.

The reconstruction part 54 further calculates a plurality of sliced images on the basis of the three-dimensional data. The plurality of sliced images shows cross-sections made by virtually slicing the patient 43 at a plurality of cross-sections different from each other, respectively. Each of the plurality of sliced images is formed of a plurality of pixels. The plurality of pixels is arranged in a matrix shape on the sliced image, and is related to brightness, respectively. The sliced images shows the cross-sections by coloring each of the plurality of pixels using the brightness related to each of the plurality of pixels.

The therapy planning part 55 displays the plurality of sliced images calculated by the reconstruction part 54 on the output device in a viewable manner for the user. The therapy planning part 55 further creates a therapy plan on the basis of information inputted by using the input device. The therapy plan shows the three-dimensional data of the patient 43, and shows a combination of a radiation angle and dose. The radiation angle shows a direction toward which the therapeutic radiation 23 is radiated to an affected portion of the patient 43, and shows a couch position, an O-ring rotation angle, and a gantry rotation angle. The couch position shows a position of the couch 41 to the base. The O-ring rotation angle shows a position of the O-ring 12 to the base. The gantry rotation angle shows a position of the traveling gantry 14 to the O-ring 12. The dose shows a dose of the therapeutic radiation 23 radiated from the respective radiation angle to the patient 43.

The radiation part 56 controls the radiotherapy apparatus 3 so that the radiotherapy shown in the therapy plan created by the therapy planning part 55 can be executed. That is, the radiation part 56 controls the couch drive device 42, controls the turn drive device 11, and controls the traveling drive device of the radiotherapy apparatus 3 so that the therapeutic radiation radiating device 16 can be arranged toward the patient 43 at the radiation angle shown in the therapy plan. The radiation part 56 further controls the first diagnostic X-ray source 24, the second diagnostic X-ray source 25, the first sensor array 32, and the second sensor array 33 so that two X-ray images of the patient 43 can be imaged. The radiation part 56 further calculates a position of the affected portion of the patient 43 on the basis of the two X-ray images, and calculates a shape of the affected portion. The radiation part 56 further controls the head swing mechanism 15 so that the therapeutic radiation radiating device 16 can face the calculated position of the affected portion. Moreover, the radiation part 56 controls the multi-leaf collimator 20 so that an irradiation field of the therapeutic radiation 23 may correspond to the shape of the affected portion. Furthermore, the radiation part 56 controls the therapeutic radiation radiating device 16 so that the therapeutic radiation 23 can be radiated to the affected portion. Further, the radiation part 56 repeatedly executes the operations from the imaging of the X-ray image to the radiating of the therapeutic radiation 23 until a dose of the therapeutic radiation 23 shown in the therapy plan is radiated to the affected portion of the patient 43.

FIG. 4 shows the imaging-timing correction data created by the imaging timing correction data creation part 51. The imaging timing correction data 61 relates the gantry angle set 62 to a first imaging timing correction amount set 63 and a second imaging timing correction amount set 64. That is, an arbitrary element of the gantry angle set 62 relates to one element of the first imaging timing correction amount set 63, and relates to one element of the second imaging timing correction amount set 64. An element of the gantry angle set 62 shows the gantry angle at which the traveling gantry 14 is arranged to the O-ring 12, and shows the gantry angle measured by the traveling drive device of the radiotherapy apparatus 3. An element relating to a certain gantry angle of the first imaging timing correction amount set 63 shows a correction amount for a timing at which the first diagnostic X-ray 35 is radiated from the first diagnostic X-ray source 24 when the gantry angle is measured by the traveling drive device of the radiotherapy apparatus 3. An element relating to a certain gantry angle of the second imaging timing correction amount set 64 shows a correction amount for a timing at which the second diagnostic X-ray 36 is radiated from the second diagnostic X-ray source 25 when the gantry angle is measured by the traveling drive device of the radiotherapy apparatus 3.

On this occasion, the imaging part 52 controls the traveling drive device of the radiotherapy apparatus 3 so that the traveling gantry 14 can rotate around the rotation axis 18 at a constant angular velocity (for example, 7 degrees per second).

The imaging part 52 calculates the gantry angle at which the traveling gantry 14 is arranged when the first diagnostic X-ray source 24 is arranged at a first imaging angle. The imaging part 52 further calculates a first imaging timing at which the traveling gantry 14 is arranged at the calculated gantry angle on the basis of the angular velocity and the measured gantry angle at which the traveling gantry 14 is arranged at a certain timing. Referring to the imaging timing correction data 61, the imaging part 52 further calculates a first corrected imaging timing on the basis of the calculated gantry angle and the first imaging timing. The first corrected imaging timing shows the timing obtained by shifting the first imaging timing by the first imaging timing correction amount relating to the gantry angle of the first imaging timing correction amount set 63. The imaging part 52 controls the first diagnostic X-ray source 24 so that the first diagnostic X-ray 35 can be radiated at the first corrected imaging timing. The imaging part 52 controls the first sensor array 32 so as to image a first image at the first imaging timing.

The imaging part 52 calculates a gantry angle at which the traveling gantry 14 is arranged when the second diagnostic X-ray source 25 is arranged at a second imaging angle. The imaging part 52 further calculates a second imaging timing at which the traveling gantry 14 is arranged at the calculated gantry angle on the basis of the angular velocity and the measured gantry angle at which the traveling gantry 14 is arranged at a certain timing. Referring to the imaging timing correction data 61, the imaging part 52 further calculates a second corrected imaging timing on the basis of the calculated gantry angle and the second imaging timing. The second corrected imaging timing shows the timing obtained by shifting the second imaging timing by the second imaging timing correction amount relating to the gantry angle of the second imaging timing correction amount set 64. The imaging part 52 controls the second diagnostic X-ray source 25 so that the second diagnostic X-ray 36 can be radiated at the second corrected imaging timing. The imaging part 52 controls the second sensor array 33 so as to image a second image at the second imaging timing.

Figure 5:
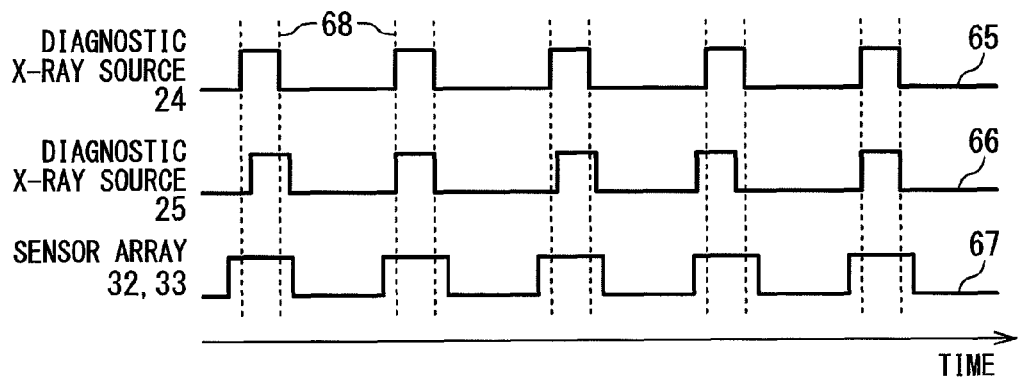
FIG. 5 is a timing chart showing operations of diagnostic X-ray sources and showing operations of sensor arrays.

FIG. 5 shows the first imaging timing calculated by the imaging part 52. The first imaging timing 68 is periodical and has a predetermined period (for example, approximately 71 msec.). FIG. 5 further shows the first corrected imaging timing calculated by the imaging part 52. The first corrected imaging timing 65 shows that the first diagnostic X-ray 35 is intermittently radiated and that the radiation of the first diagnostic X-ray 35 is stopped after the first diagnostic X-ray 35 is radiated for a predetermined period (for example, 10 msec.). The first corrected imaging timing 65 substantially coincides to the first imaging timing 68, which shows the timing is shifted by the first imaging timing correction amount calculated by the imaging part 52.

FIG. 5 further shows the second imaging timing calculated by the imaging part 52. The second corrected imaging timing coincides to the first imaging timing 68. FIG. 5 further shows the second corrected imaging timing calculated by the imaging part 52. The second corrected imaging timing 66 shows that the second diagnostic X-ray 36 is intermittently radiated and that the radiation of the second diagnostic X-ray 36 is stopped after the second diagnostic X-ray 36 is radiated for a predetermined period (for example, 10 msec.). The second corrected imaging timing 66 substantially coincides to the second imaging timing, which shows the timing is shifted by the second imaging timing correction amount calculated by the imaging part 52.

FIG. 5 further shows the timing at which the first sensor array 32 receives the X-ray to image an X-ray image. The timing 67 shows that the first sensor array 32 stops the receiving after receiving the X-ray for a predetermined sensing time and that the receiving is periodical and has the period of the first imaging timing 68. FIG. 5 further shows the timing at which the second sensor array 33 receives the X-ray to image an X-ray image. The timing coincides to the timing 67, that is, shows that the second sensor array 33 stops the receiving after receiving the X-ray for the predetermined sensing time and that the receiving is periodical and has the period of the second imaging timing. The sensing time is designed so that a period for the radiation of the first diagnostic X-ray 35 may be constantly included in the sensing time and so that a period for the radiation of the second diagnostic X-ray 36 may be constantly included in the sensing time.

Figure 6:
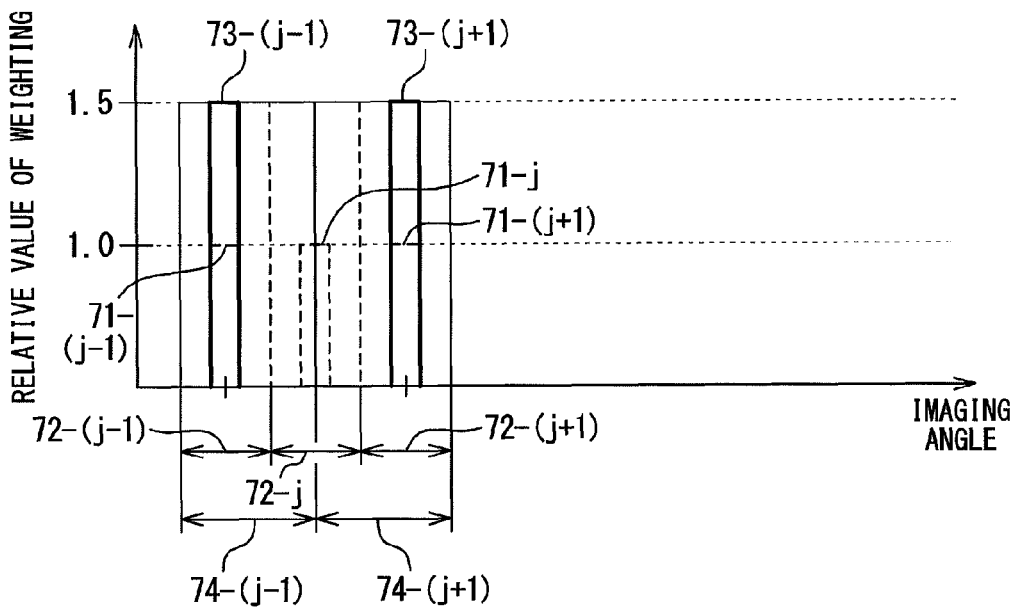
FIG. 6 is a graph showing a plurality of weightings.

FIG. 6 shows the plurality of weightings calculated by the weighting calculation part 53. The plurality of weightings 71-($j$−1) to 71-($j$+1) is related to a plurality of X-ray images. The plurality of X-ray images belongs to any of a plurality of sections provided by dividing the imaging angle range. It is shown that the plurality of weightings 71-($j$−1) to 71-($j$+1) indicates the same value (for example, 1) in a case where each of the plurality of X-ray images belongs to continuous partial sections 72-($j$−1) to 72-($j$+1) of the plurality of sections and where the lengths of the sections 72-($j$−1) to 72-($j$+1) are same each other.

FIG. 6 further shows the plurality of weightings calculated by the weighting calculation part 53 in a case where one X-ray image of the plurality of X-ray images imaged by the imaging part 52 is absent. The plurality of weightings 73-($j$−1) and 73-($j$+1) are related to two X-ray images imaged at two imaging angles adjacent to the imaging angle at which the absent X-ray image has been imaged. On this occasion, the section to which the absent X-ray image belongs is deleted, and the lengths of the two sections 74-($j$−1) and 74-($j$+1) to which the two X-ray image belong respectively are extended by the length of the section of the absent X-ray image. For example, it is shown that the length of the section after the section deletion is 1.5 times as long as that of the section before the section deletion. At this time, the plurality of weightings 73-($j$−1) and 73-($j$+1) are increased in proportion to extension ratios of the lengths of the sections 74-($j$−1) and 74-($j$+1). That is, the plurality of weightings 73-($j$−1) and 73-($j$+1) shows values 1.5 times as large as those of the plurality of weightings 71-($j$−1) to 71-($j$+1).

According to this weighting calculation, density of the imaging data (information amount of the image per unit angle) becomes even in the imaging angle range, the reconstruction part 54 reconstructs the plurality of X-ray images on the basis of the weightings, and thus the three-dimensional data can be calculated more accurately.

Figure 7:
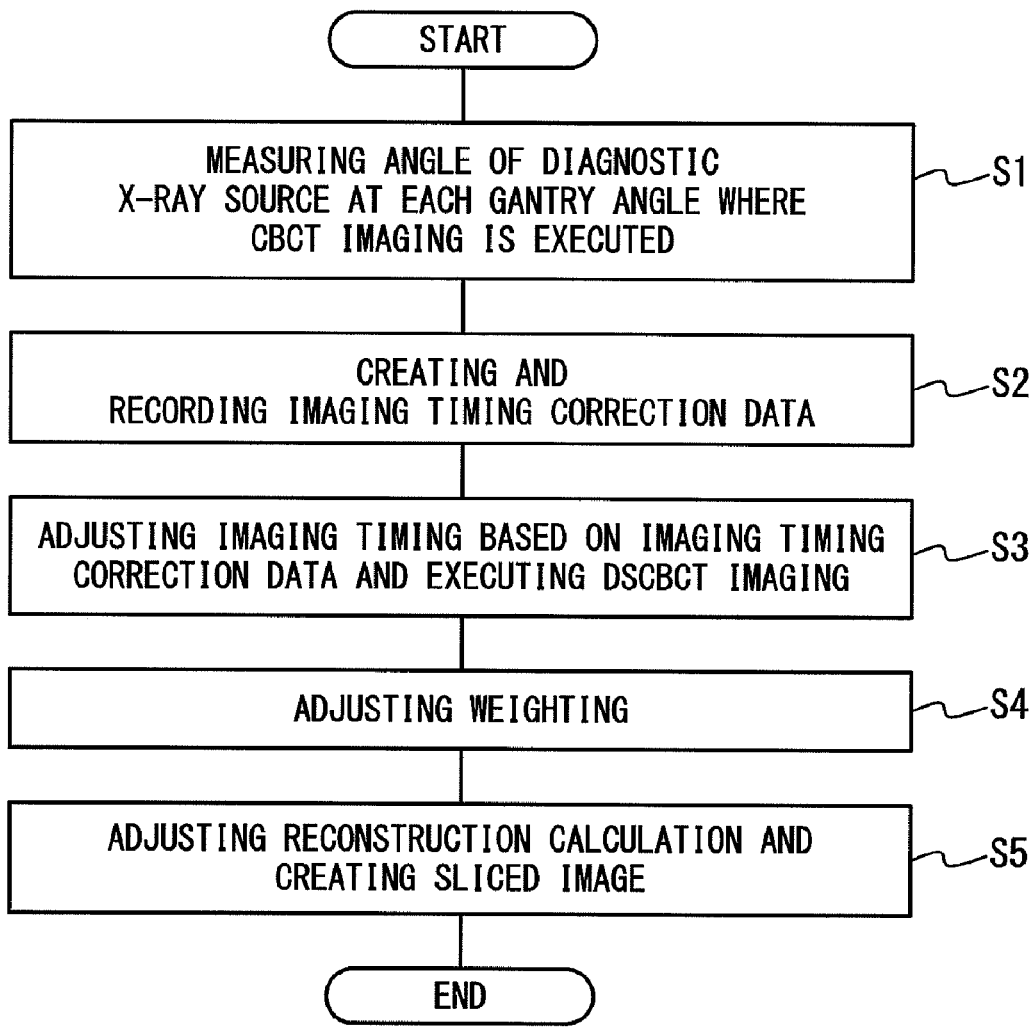
FIG. 7 is a flowchart showing a radiation tomography method according to the present invention.

FIG. 7 shows an embodiment of a radiation tomography method according to the present invention. At first, a user operates the radiotherapy apparatus control device 2 so that the traveling gantry 14 can be arranged at each of the plurality of gantry angles. The user measures the first measurement angle at which the first diagnostic X-ray source 24 is arranged to the O-ring 12 and measures the second measurement angle at which the second diagnostic X-ray source 25 is arranged to the O-ring 12, every time when the traveling gantry 14 is arranged at each of the plurality of gantry angles. The user creates the deflection data on the basis of the measurement result, and input the deflection data to the radiotherapy apparatus control device 2 (step S1). The radiotherapy apparatus control device 2 creates the imaging timing correction data 61 on the basis of the deflection data, and records the imaging timing correction data 61 to the storage device (step S2).

The user fixes the patient 43 to the couch 41 of the radiotherapy apparatus 3. The user input the turn angle, the plurality of first imaging angles, and the plurality of second imaging angles to the radiotherapy apparatus control device 2. The radiotherapy apparatus control device 2 controls the turn drive device 11 so that the O-ring 12 can be arranged at the turn angle to the base. The radiotherapy apparatus control device 2 controls the traveling drive device of the radiotherapy apparatus 3 so that the traveling gantry 14 can rotate around the rotation axis 18 at a constant velocity angle (for example, 7 degrees per second). The radiotherapy apparatus control device 2 calculates the gantry angle at which the traveling gantry 14 is arranged when the first diagnostic X-ray source 24 is arranged at the first imaging angle, and calculates the gantry angle at which the traveling gantry 14 is arranged when the second diagnostic X-ray source 25 is arranged at the second imaging angle. The radiotherapy apparatus control device 2 further calculates the first imaging timing or the second imaging timing at which the traveling gantry 14 is arranged at the calculated gantry angle.

Referring to the imaging timing correction data 61, the radiotherapy apparatus control device 2 further calculates the first corrected imaging timing on the basis of the calculated gantry angle and the first imaging timing. The first corrected imaging timing shows the timing obtained by shifting the first imaging timing by the first imaging timing correction amount related to the gantry angle of the first imaging timing correction amount set 63. Referring to the imaging timing correction data 61, the radiotherapy apparatus control device 2 further calculates the second corrected imaging timing on the basis of the calculated gantry angle and the second imaging timing. The second corrected imaging timing shows the timing obtained by shifting the second imaging timing by the second imaging timing correction amount related to the gantry angle of the second imaging timing correction amount set 64.

The radiotherapy apparatus control device 2 controls the first diagnostic X-ray source 24 so that the first diagnostic X-ray 35 can be radiated at the first corrected imaging timing. The radiotherapy apparatus control device 2 controls the first sensor array 32 so as to image the first image at the first imaging timing. The radiotherapy apparatus control device 2 controls the second diagnostic X-ray source 25 so that the second diagnostic X-ray 36 can be radiated at the second corrected imaging timing. The radiotherapy apparatus control device 2 controls the second sensor array 33 so as to image the second image at the second imaging timing (step S3).

The radiotherapy apparatus control device 2 calculates the plurality of weightings on the basis of the first image and the second image so that density of the imaging data (information amount of the image per unit angle) may become even in the imaging angle range (step S4). The radiotherapy apparatus control device 2 calculates three-dimensional data on the basis of the plurality of first images, the plurality of second images, and the plurality of weightings. The reconstruction part 54 further calculates the plurality of sliced images on the basis of the three-dimensional data (step S5).

The traveling gantry 14 deflects because of mass of the therapeutic radiation radiating device 16, the multi-leaf collimator 20, the first diagnostic X-ray source 24, the second diagnostic X-ray source 25, and the like, and an amount of the deflection varies depending on the gantry angle. According to the radiation tomography method of the present invention, even in the case where the traveling gantry 14 deflects in the amount varying depending on the gantry angle, the radiotherapy apparatus control device 2 can accurately calculates timings at which the first diagnostic X-ray source 24 and the second diagnostic X-ray source 25 are arranged at predetermined angles, and accordingly the radiotherapy apparatus 3 can radiate the first diagnostic X-ray 35 and the second diagnostic X-ray 36 from more accurate positions to the patient 43. In this manner, the radiotherapy apparatus control device 2 can image the X-ray image of the patient 43 by using the first diagnostic X-ray 35 and the second diagnostic X-ray 36 from the plurality of imaging angles dividing the imaging angle range more accurately in equal intervals, and the three-dimensional data of the patient 43 can be calculated more accurately by reconstructing the X-ray image.

The radiotherapy system 1 further carries out an operation for creating a therapy plan and an operation of the radiotherapy.

In the operation for creating the therapy plan, the radiotherapy apparatus control device 2 displays the plurality of sliced images calculated by the radiation tomography method of the present invention. The user views the images, specifies a position and a shape of the affected portion, and inputs the position and the shape of the affected portion to the radiotherapy apparatus control device 2. The radiotherapy apparatus control device 2 creates a therapy plan on the basis of the position and the shape of the affected portion. The therapy plan shows three-dimensional data of the patient 43, and shows a combination of the radiation angle and the dose. The radiation angle shows a direction to which the therapeutic radiation 23 is radiated to the affected portion of the patient 43, and shows the couch position, the O-ring rotation angle, and the gantry rotation angle. The couch position shows the position of the couch 41 to the base. The O-ring rotation angle shows the position of the O-ring 12 to the base. The gantry rotation angle shows the position of the traveling gantry 14 to the O-ring 12. The dose shows the dose of the therapeutic radiation 23 radiated from the respective radiation angles to the patient 43.

In the operation of the radiotherapy, the radiotherapy apparatus control device 2 controls the radiotherapy apparatus 3 so that the dose of the therapeutic radiation 23 shown in the therapy plan can be radiated to the patient 43 from the radiation angle shown by the therapy plan. That is, the radiotherapy apparatus control device 2 controls the couch drive device 42 so that the couch 41 can be arranged on the couch position shown in the therapy plan. The radiotherapy apparatus control device 2 controls the turn drive device 11 so that the O-ring 12 can be arranged at the O-ring rotation angle shown in the therapy plan. The radiotherapy apparatus control device 2 further controls the traveling drive device of the radiotherapy apparatus 3 so that the traveling gantry 14 can be arranged at the gantry rotation angle shown in the therapy plan.

The radiotherapy apparatus control device 2 controls the first diagnostic X-ray source 24 so that the first diagnostic X-ray 35 can be radiated. The radiotherapy apparatus control device 2 controls the first sensor array 32 so that the first X-ray image can be imaged on the basis of the transmitted radiation after the radiated first diagnostic X-ray 35 transmitted through the patient 43. The radiotherapy apparatus control device 2 controls the second diagnostic X-ray source 25 so that the second diagnostic X-ray 36 can be radiated. The radiotherapy apparatus control device 2 controls the second sensor array 33 so that the second X-ray image can be imaged on the basis of the transmitted radiation after the radiated second diagnostic X-ray 36 transmitted through the patient 43.

The radiotherapy apparatus control device 2 calculates the position and the shape of the affected portion of the patient 43 on the basis of the first X-ray image and the second X-ray image. The radiotherapy apparatus control device 2 controls the head swing mechanism 15 so that the therapeutic radiation radiating device 16 can face the calculated position. The radiotherapy apparatus control device 2 controls the multi-leaf collimator 20 so that the irradiation field of the therapeutic radiation 23 can be the same shape as that of the affected portion. Furthermore, the radiotherapy apparatus control device 2 controls the therapeutic radiation radiating device 16 so that the therapeutic radiation 23 can be radiated to the affected portion. Further, the radiotherapy apparatus control device 2 repeatedly executes the operations from the imaging of X-ray image to the radiation of the therapeutic radiation 23 until the dose of the therapeutic radiation 23 shown in the therapy plan is radiated to the affected portion of the patient 43. For example, the period can be 0.2 seconds.

The position and the shape of the affected portion of the patient 43 calculated on the basis of the first X-ray image and the second X-ray image are more accurate compared to the position and the shape calculated on the basis of two X-ray images respectively imaged by using two imager arranged around the isocenter 19 at other angles than the perpendicularity. For this reason, the radiotherapy apparatus 3 can carry out the radiotherapy more accurately compared to another radiotherapy apparatus having two imagers arranged at other angles than the perpendicularity.

Figure 8:
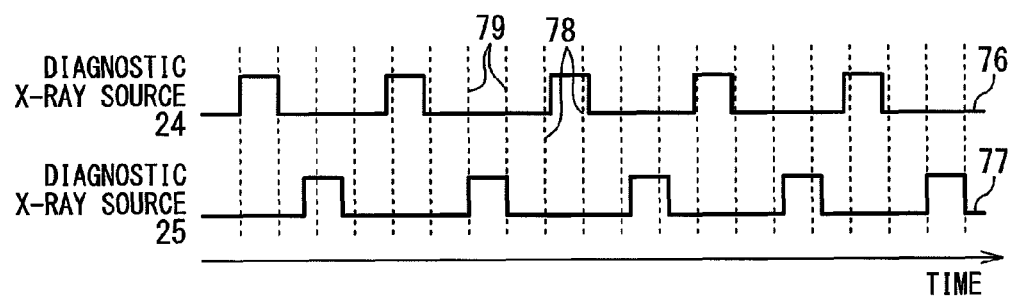
FIG. 8 is a timing chart showing an operation of a diagnostic X-ray source.

In another embodiment of the radiation tomography method of the present invention, the first imaging timing 68 in the above-mentioned embodiment is replaced by another first imaging timing, and the second imaging timing is replaced by another second imaging timing. As shown in FIG. 8, the first imaging timing 78 is periodical and has a predetermined period (for example, approximately 71 msec.). The second imaging timing 79 is periodical and has the period shown by the first imaging timing 78, and the phase is shifted from the phase of the first imaging timing 78 by a half of the period.

FIG. 8 further shows the first corrected imaging timing calculated by the imaging part 52. The first corrected imaging timing 76 shows that the first diagnostic X-ray 35 is intermittently radiated and that the radiation of the first diagnostic X-ray 35 is stopped after the first diagnostic X-ray 35 is radiated for a predetermined period (for example, 10 msec.). The first corrected imaging timing 76 substantially coincides to the first imaging timing 68, and shows the timing is shifted by the first imaging timing correction amount calculated by the imaging part 52.

FIG. 8 further shows the second corrected imaging timing calculated by the imaging part 52. The second corrected imaging timing 77 shows that the second diagnostic X-ray 36 is intermittently radiated and that the radiation of the second diagnostic X-ray 36 is stopped after the second diagnostic X-ray 36 is radiated for a predetermined period (for example, 10 msec.). The second corrected imaging timing 77 substantially coincides to the second imaging timing 52, and shows the timing is shifted by the second imaging timing correction amount calculated by the imaging part 52.

According to such first imaging timing 78 and the second imaging timing 79, compared to a technique not correcting the imaging timing in each imaging, the three-dimensional data of the patient 43 can be calculated more accurately in the same manner as the radiation tomography method according to the above-mentioned embodiment. Moreover, according to such first imaging timing 78 and the second imaging timing 79, the sensing time of the first sensor array 32 can be controlled so that the first sensor array 32 can receive only the transmitted radiation of the first diagnostic X-ray 35 without receiving the scattered radiation of the second diagnostic X-ray 36, and the second sensor array 33 can be controlled so that the second sensor array 33 can receive only the transmitted radiation of the second diagnostic X-ray 36 without receiving the scattered radiation of the first diagnostic X-ray 35. On this occasion, the plurality of X-ray images imaged by the first sensor array 32 or the second sensor array 33 reduces influence of the scattered radiation, and is clearer. As the result, the three-dimensional data calculated on the basis of the plurality of X-ray images become clearer, and becomes more accurate.

Figure 9:
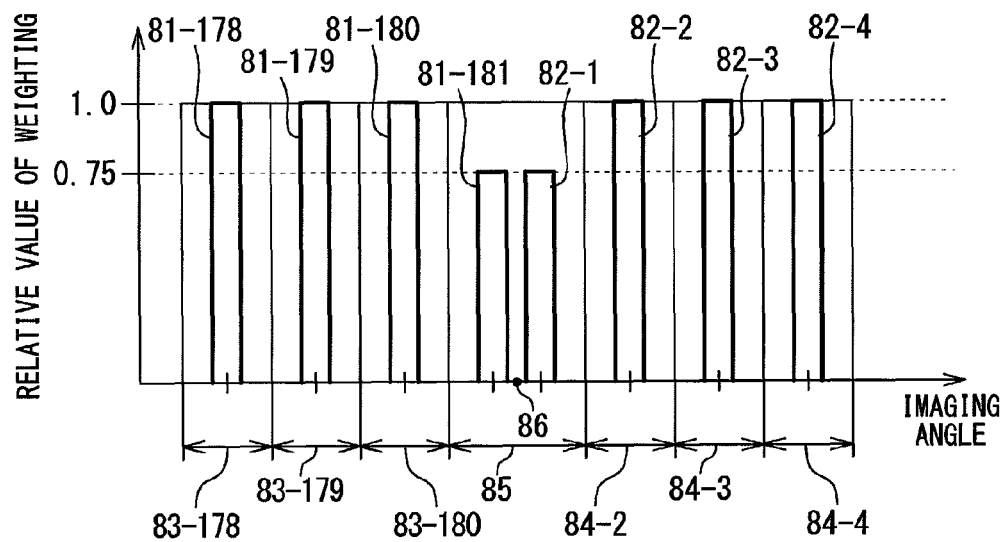
FIG. 9 is a graph showing a plurality of weightings.

FIG. 9 shows a plurality of weightings calculated by the weighing calculation part 53 when such first imaging timing 78 and second imaging timing 79 are applied. A plurality of weightings 81-178 to 81-181 is related to a plurality of second X-ray images imaged by the second sensor array 33, and the plurality of weightings 82-1 to 82-4 is related to the plurality of first X-ray images imaged by the first sensor array 32. The plurality of weightings 81-178 to 81-181 shows that each imaging angle at which each second X-ray image has been imaged is represented by (0.5×n) degrees (n: integer). The plurality of weightings 82-1 to 82-4 shows that each imaging angle at which each first X-ray image has been imaged is represented by (0.5×n+0.25) degrees. The plurality of weightings 81-178 to 81-181 and the plurality of weightings 82-1 to 82-4 show that an interval between the imaging angle at which the second X-ray image related to the weighting 81-181 has been imaged and the imaging angle at which the first X-ray image related to the weighting 82-1 has been imaged is 0.25, the interval is different from the interval 0.5 degrees of the imaging angle of the first X-ray image, and the interval is different from the interval 0.5 degrees of the imaging angle of the second X-ray image. That is, the plurality of weightings 81-178 to 81-181 and the plurality of weightings 82-1 to 82-4 show that, when the first imaging timing 78 and the second imaging timing 79 are applied, the interval of the imaging angle is different from other intervals at a boundary 86 between a range of the imaging angles at which the first X-ray image is imaged and a range of the imaging angles at which the second X-ray image is imaged.

FIG. 9 further shows a plurality of sections to which the first X-ray image and the second X-ray image belong. To the plurality of sections 83-178 to 83-180, the plurality of second X-ray images related to the plurality of weightings 81-178 to 81-181 belong, respectively. To a plurality of sections 84-2 to 84-4, the plurality of first X-ray images related to the plurality of weightings 82-2 to 82-4 belongs, respectively. To the section 85, the second X-ray image related to the weighting 81-181 and the first X-ray image related to the weighting 82-1 belong.

It is shown that the length of the section 85 is longer than that of each of the plurality of sections 83-178 to 83-180 and 84-2 to 84-4 and is 1.5 times as long as that of each of the plurality of sections 83-178 to 83-180 and 84-2 to 84-4. It is shown that each of the weightings 81-181 and the weighting 82-1 is smaller than each of the weightings 81-178 to 81-180 and 82-2 to 82-4, and is 0.75 times as small as each of the weightings 81-178 to 81-180 and 82-2 to 82-4. On this occasion, the density of the imaging data (information amount of the image per unit angle) becomes even in the imaging angle range, the reconstruction part 54 reconstructs the plurality of X-ray images on the basis of the weightings, and thus the three-dimensional data can be calculated more accurately. That is, according to this weighting calculation, the three-dimensional data can be calculated more accurately even in a case where the first imaging timing 78 and the second imaging timing 79 are applied.

Figure 10:
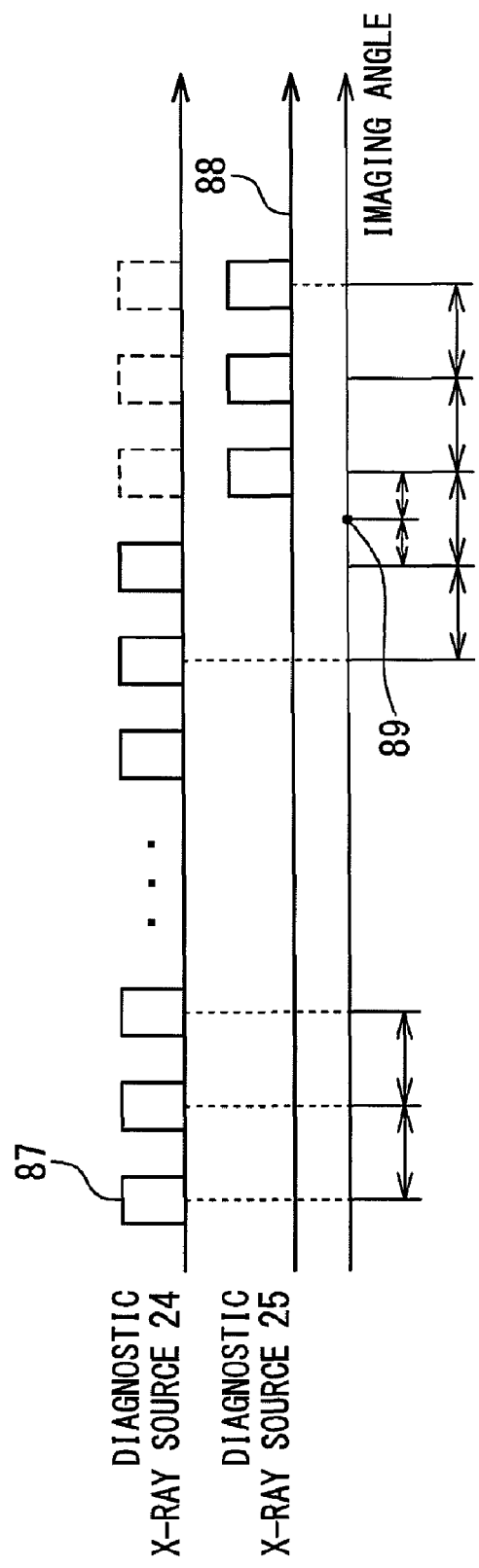
FIG. 10 is a timing chart showing an operation of a diagnostic X-ray source.

In further another embodiment of the radiation tomography method of the present invention, the imaging angles of the plurality of X-ray images imaged at the first corrected imaging timing 76 and the second corrected imaging timing 77 according to the above-mentioned embodiment are replaced by other imaging angles. FIG. 10 shows a first imaging angle at which the first diagnostic X-ray source 24 is arranged when the first diagnostic X-ray 35 is radiated at the first corrected imaging timing 76. The first imaging angle 88 shows that the plurality of imaging angles at which the first diagnostic X-ray source 24 is arranged at the first corrected imaging timing 76 divides a part of the imaging angle range in equal intervals, each having a predetermined interval $\Delta\theta$. FIG. 10 further shows a second imaging angle at which the first diagnostic X-ray source 24 is arranged when the second diagnostic X-ray 36 is radiated at the second corrected imaging timing 77. The second imaging angle 87 shows that the plurality of imaging angles at which the second diagnostic X-ray source 25 is arranged at the second corrected imaging timing 77 divides a part of the imaging angle range in equal intervals, each having a predetermined interval $\Delta\theta$.

In the vicinity of a boundary 89 between a range of the imaging angles at which the first X-ray image is imaged and a range of the imaging angles at which the second X-ray image is imaged, the first imaging angle 88 further shows that the imaging angle at which the first diagnostic X-ray source 24 is arranged when the first diagnostic X-ray 35 is radiated is shifted by only Δθ/2 from the boundary 89. The second imaging angle 87 further shows the imaging angle at which the second diagnostic X-ray source 25 is arranged when the second diagnostic X-ray 36 is radiated in the vicinity of the boundary 89 is shifted by only Δθ/2 from the boundary 89. The first imaging angle 88 and the second imaging angle 87 shows that a difference between the imaging angle at which the first diagnostic X-ray source 24 is arranged when the first diagnostic X-ray 35 is radiated in the vicinity of the boundary 89 and the imaging angle at which the second diagnostic X-ray source 25 is arranged when the second diagnostic X-ray 36 is radiated in the vicinity of the boundary 89 is Δθ. That is, the first imaging angle 88 and the second imaging angle 87 show that the plurality of imaging angles at which the first diagnostic X-ray 35 and the second diagnostic X-ray 36 are radiated respectively divide all of the imaging angle range in equal intervals of Δθ.

This interval Δθ is calculated by solving the following expression:

$$n = (\theta_{open} - \Delta\theta/2)/\Delta\theta.$$

Here, the integral number n is arbitrary integer number, the angle θopen is an angle between the first diagnostic X-ray source 24 and the second diagnostic X-ray source 25. For example, the interval Δθ is about 0.4986149 degrees when n=180 and θopen=90 degrees. The interval Δθ is 20 degrees when n=4 and θopen=90 degrees. On this occasion, the first imaging angle 88 is 100 degrees, 120 degrees, 140 degrees, 160 degrees, 180 degrees, and 200 degrees, and the second imaging angle 87 is 0 degrees, 20 degrees, 40 degrees, 60 degrees, and 80 degrees.

According to the radiation tomography method to which the plurality of imaging angles are applied, the three-dimensional data can be calculated more accurately in the same manner as that of the above-mentioned radiation tomography method as shown in FIG. 9 to which the plurality of imaging angles are applied. According to the radiation tomography method to which the plurality of imaging angles are applied, compared to the above-mentioned radiation tomography method to which the plurality of imaging angles are applied as shown in FIG. 9, the three-dimensional data can be calculated more accurately by using a plurality of X-ray images imaged from the plurality of imaging angles dividing the imaging angle range in more equal intervals.

Meanwhile, in the radiation tomography method to which a plurality of such imaging angles are applied, the first diagnostic X-ray source 24 can be controlled so that the first diagnostic X-ray 35 can be radiated at the first corrected imaging timing and the second diagnostic X-ray source 25 can be controlled so that the second diagnostic X-ray 36 can be radiated at the second corrected imaging timing, without correcting the first imaging timing or the second imaging timing calculated on the basis of the plurality of imaging angles. According to this radiation tomography method, compared to the above-mentioned radiation tomography method to which the plurality of imaging angles are applied as shown in FIG. 9, the three-dimensional data can be calculated more accurately when a deflection amount of the traveling gantry 14 is quite small, which is useful.

Moreover, the radiation tomography method of the present invention can be applied to another radiotherapy apparatus having n imager systems. On this occasion, n diagnostic X-ray sources are arranged on positions where an angle between two line segments connecting two adjoining diagnostic X-ray sources of the n diagnostic X-ray sources to the isocenter 19 becomes (180/n) degrees.

Figure 11:
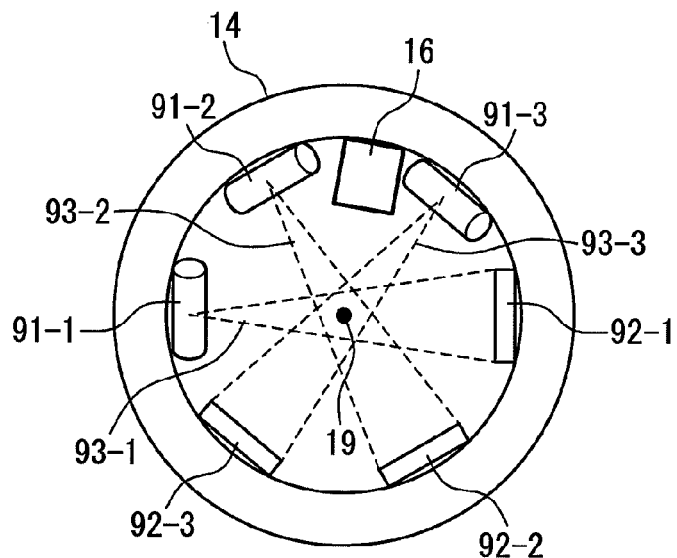
FIG. 11 is a view showing another radiotherapy apparatus.

FIG. 11 shows the radiotherapy apparatus. In the radiotherapy apparatus, the imager system of the radiotherapy apparatus 3 according to the above-mentioned embodiment is replaced by another imager system. That is, the radiotherapy apparatus includes diagnostic X-ray sources 91-1 to 91-3 and sensor arrays 92-1 to 92-3, wherein n=3. The diagnostic X-ray sources 91-1 to 91-3 are supported by the traveling gantry 14 and are arranged inside the ring of the traveling gantry 14, respectively. The diagnostic X-ray source 91-2 is arranged on a position where an angle between a line segment connecting the isocenter 19 to the diagnostic X-ray source 91-1 and a line segment connecting the isocenter 19 to the diagnostic X-ray source 91-2 is 60 degrees. The diagnostic X-ray source 91-3 is arranged on a position where an angle between a line segment connecting the isocenter 19 to the diagnostic X-ray source 91-2 and a line segment connecting the isocenter 19 to the diagnostic X-ray source 91-3 is 60 degrees. The diagnostic X-ray source 91-1 is controlled by the radiotherapy apparatus control device 2 to radiate diagnostic X-ray 93-1 toward the isocenter 19. The diagnostic X-ray source 91-2 is controlled by the radiotherapy apparatus control device 2 to radiate the diagnostic X-ray 93-2 toward the isocenter 19. The diagnostic X-ray source 91-3 is controlled by the radiotherapy apparatus control device 2 to radiate diagnostic X-ray 93-3 toward the isocenter 19.

Figure 12:
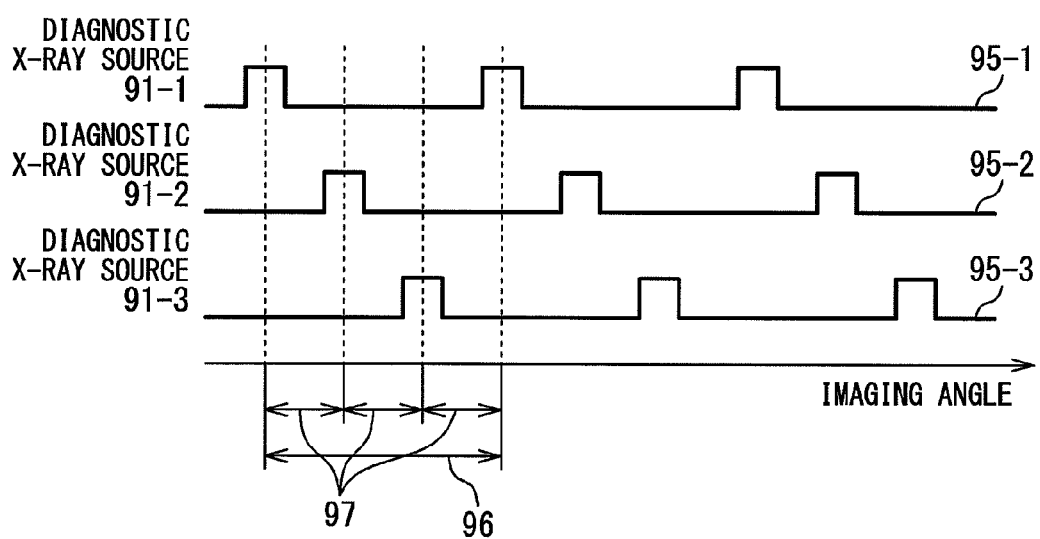
FIG. 12 is a timing chart showing an operation of a diagnostic X-ray source.

FIG. 12 shows the plurality of imaging timings that are converted from the first imaging timing 68 and the second imaging timing in the above-mentioned embodiment when the radiation tomography method of the present invention is applied to this radiotherapy apparatus. A plurality of imaging timings 95-1 to 95-3 are periodical and has a predetermined period 96 (for example, approximately 71 msec.). The phase of the imaging timing 95-2 is shifted by one-third of the period 96 from the phase of the imaging timing 95-1. The phase of the imaging timing 95-3 is shifted by two-third of the period 96 from the phase of the imaging timing 95-1. That is, most part of the imaging timing 95-2 coincides to the timing whose phase delays by one-third period 97 from the imaging timing 95-1. The one-third period 97 shows a quotient obtained by dividing the period 96 by 3. Most part of the imaging timing 95-3 coincides to the timing whose phase delays by one-third period 97 from the imaging timing 95-2. Most part of the imaging timing 95-1 coincides to the timing whose phase delays by one-third period 97 from the imaging timing 95-3.

At this time, the imaging timing correction data 61 is converted into other imaging timing correction data that further relates the gantry angle set 62 to the third imaging timing correction amount set. Referring to the imaging timing correction data, the radiotherapy apparatus control device 2 corrects the plurality of imaging timings 95-1 to 95-3 to the plurality of corrected imaging timings, controls the diagnostic X-ray sources 91-1 to 91-3 so that the plurality of diagnostic X-rays 93-1 to 93-3 can be radiated at the plurality of corrected imaging timings respectively, and controls the sensor arrays 92-1 to 92-3 so that the plurality of X-ray images can be imaged at the plurality of corrected imaging timings. The radiotherapy apparatus control device 2 calculates the plurality of weightings on the basis of the plurality of X-ray images, calculates the three-dimensional data on the basis of the plurality of X-ray images and the plurality of weightings, and calculates the plurality of sliced images.

According to the radiation tomography method applied to this radiotherapy apparatus, the three-dimensional data can be calculated with high accuracy in the same manner as that of the above-mentioned radiation tomography method. Compared to the above-mentioned radiation tomography method, the radiation tomography method applied to this radiotherapy apparatus further can image the plurality of X-ray images in shorter time, which is preferable.

The invention claimed is:

1. A radiation tomography method comprising:
calculating a radiating timing, with reference to imaging timing correction data relating a plurality of gantry angles to a plurality of imaging timing correction amounts, on the basis of (i) an imaging timing at which a radiation source supported by a rotating traveling gantry is arranged at a predetermined imaging angle and (ii) an imaging timing correction amount, included in the plurality of imaging timing correction amounts, related to a gantry angle at which the rotating traveling gantry is arranged at the imaging timing;
calculating, on the basis of an X-ray image obtained with a radiation radiated from the radiation source at the radiating timing, three-dimensional data of the X-ray image; and
calculating a plurality of weightings related to a plurality of X-ray images to be reconstructed as the three-dimensional data on the basis of the X-ray image and the predetermined imaging angle,
wherein the radiation source radiates the radiation without rotating more than once during imaging to obtain the X-ray image,
wherein the plurality of X-ray images is related to a plurality of imaging angles,
wherein the plurality of weightings is calculated so that, when in-unit-angle X-ray images included in the plurality of X-ray images are related to in-unit-angle imaging angles included in an unit angle range, a summation of in-unit-angle weightings related to the in-unit-angle X-ray images is even, the in-unit-angle weightings being included in the plurality of weightings, and
wherein the three-dimensional data is further calculated on the basis of the plurality of weightings.

2. The radiation tomography method according to claim 1, further comprising:
calculating another radiating timing,
wherein the imaging timing correction data further relates the plurality of gantry angles to a plurality of other imaging timing correction amounts,
wherein the another radiating timing is calculated on the basis of (i) another imaging timing at which another radiation source supported by the rotating traveling gantry is arranged at another predetermined imaging angle and (ii) another imaging timing correction amount, included in plurality of other imaging timing correction amounts, related to another gantry angle at which the rotating traveling gantry is arranged at the other imaging timing, and
wherein the three-dimensional data is further calculated on the basis of another X-ray image obtained with another radiation radiated at the other radiating timing from the other radiation source.

3. The radiation tomography method according to claim 2, wherein the other radiation is radiated in a period when the radiation is not radiated, and
wherein the radiation is radiated in a period when the other radiation is not radiated.

4. The radiation tomography method according to claim 3, wherein the predetermined imaging angle and the other predetermined imaging angle are formed so as to coincide with any one of a plurality of imaging angles having equal intervals.

5. The radiation tomography method according to claim 2, further comprising:
measuring a plurality of first absolute angles at which the radiation source is arranged when the rotating traveling gantry is arranged at the plurality of gantry angles;
measuring a plurality of second absolute angles at which the other radiation source is arranged when the rotating traveling gantry is arranged at the plurality of gantry angles; and
creating the imaging timing correction data on the basis of the plurality of first absolute angles and the plurality of second absolute angles.

6. A non-transitory computer readable recording medium which records thereon a computer program, wherein, when executed, the computer program causes a computer to execute a radiation tomography method comprising:
calculating a radiating timing, with reference to imaging timing correction data relating a plurality of gantry angles to a plurality of imaging timing correction amounts, on the basis of (i) an imaging timing at which a radiation source supported by a rotating traveling gantry is arranged at a predetermined imaging angle and (ii) an imaging timing correction amount, included in the plurality of imaging timing correction amounts, related to a gantry angle at which the rotating traveling gantry is arranged at the imaging timing;
calculating, on the basis of an X-ray image obtained with a radiation radiated from the radiation source at the radiating timing, three-dimensional data of the X-ray image; and
calculating a plurality of weightings related to a plurality of X-ray images to be reconstructed as the three-dimensional data on the basis of the X-ray image and the predetermined imaging angle,
wherein the radiation source radiates the radiation without rotating more than once during imaging to obtain the X-ray image,
wherein the plurality of X-ray images is related to a plurality of imaging angles,
wherein the plurality of weightings is calculated so that, when in-unit-angle X-ray images included in the plurality of X-ray images are related to in-unit-angle imaging angles included in an unit angle range, a summation of in-unit-angle weightings related to the in-unit-angle X-ray images is even, the in-unit-angle weightings being included in the plurality of weightings, and
wherein the three-dimensional data is further calculated on the basis of the plurality of weightings.

7. The non-transitory computer readable recording medium according to claim 6, wherein the radiation tomography method further comprises:
calculating another radiating timing,
wherein the imaging timing correction data further relates the plurality of gantry angles to a plurality of other imaging timing correction amounts,
wherein the other radiating timing is calculated on the basis of (i) another imaging timing at which another radiation source supported by the rotating traveling gantry is arranged at another predetermined imaging angle and (ii) another imaging timing correction amount, included in the plurality of other imaging timing correction amounts, related to another gantry angle at which the rotating traveling gantry is arranged at the other imaging timing, and wherein the three-dimensional data is further calculated on the basis of another X-ray image obtained with another radiation radiated at the other radiating timing from the other radiation source.

8. The non-transitory computer readable recording medium according to claim 7,
wherein the other radiation is radiated in a period when the radiation is not radiated, and
wherein the radiation is radiated in a period when the other radiation is not radiated.

9. The non-transitory computer readable recording medium according to claim 8, wherein the predetermined imaging angle and the other predetermined another imaging angle are formed so as to coincide with any one of a plurality of imaging angles having equal intervals.

10. The non-transitory computer readable recording medium according to claim 7, wherein the radiation tomography method further comprises:
measuring a plurality of first absolute angles at which the radiation source is arranged when the rotating traveling gantry is arranged at the plurality of gantry angles;
measuring a plurality of second absolute angles at which the other radiation source is arranged when the rotating traveling gantry is arranged at the plurality of gantry angles; and
creating the imaging timing correction data on the basis of the plurality of first absolute angles and the plurality of second absolute angles.

11. A radiotherapy apparatus control device, comprising:
an imaging part configured to obtain an X-ray image, with reference to imaging timing correction data relating a plurality of gantry angle to a plurality of imaging timing correction amounts, by causing a radiation source to radiate a radiation at a radiating timing calculated on the basis of (i) an imaging timing at which the radiation source supported by a rotating traveling gantry is arranged at a predetermined imaging angle and (ii) an imaging timing correction amount, included in the plurality of imaging timing correction amounts, related to a gantry angle at which the rotating traveling gantry is arranged at the imaging timing;
a reconstruction part configured to calculate three-dimensional data of the X-ray image on the basis of the X-ray image; and
a weighting calculation part configured to calculate a plurality of weightings related to a plurality of X-ray images to be reconstructed as the three-dimensional data on the basis of the X-ray image and the predetermined imaging angle,
wherein the radiation source radiates the radiation without rotating more than once during imaging to obtain the X-ray image,
wherein the plurality of X-ray images is related to a plurality of imaging angles,
wherein the plurality of weightings is calculated so that, when in-unit-angle X-ray images included in the plurality of X-ray images are related to in-unit-angle images included in a unit angle range, a summation of in-unit-angle weightings related to the in-unit-angle X-ray images is even, the in-unit-angle weightings being included in the plurality of weightings, and
wherein the reconstruction part further calculates the three-dimensional data on the basis of the plurality of weightings.

12. The radiotherapy apparatus control device according to claim 11,
wherein the imaging timing correction data further relates the plurality of gantry angles to a plurality of other imaging timing correction amounts,
wherein the imaging part (i) calculates another radiating timing on the basis of (a) another imaging timing at which another radiation source supported by the rotating traveling gantry is arranged at another predetermined imaging angle and (b) another imaging timing correction amount, included in the plurality of other imaging timing correction amounts, related to another gantry angle at which the rotating traveling gantry is arranged at the other imaging timing, and (ii) obtains another X-ray image by causing the other radiation source to radiate another radiation at the other radiating timing, and
wherein the reconstruction part further calculates the three-dimensional data on the basis of the other X ray image.

13. The radiotherapy apparatus control device according to claim 12,
wherein the other radiation is radiated in a period when the radiation is not radiated, and
wherein the radiation is radiated in a period when the other radiation is not radiated.

14. The radiotherapy apparatus control device according to claim 13, wherein the predetermined imaging angle and the other predetermined imaging angle are formed so as to coincide with any one of a plurality of imaging angles having equal intervals.

15. The radiotherapy apparatus control device according to claim 12, further comprising:
an imaging timing correction data creation part configured to create the imaging timing correction data on the basis of (i) a plurality of first absolute angles of the radiation source measured when the rotating traveling gantry is arranged at the plurality of gantry angles and (ii) a plurality of second absolute angles of the other radiation source measured when the rotating traveling gantry is arranged at the plurality of gantry angles.

16. A radiotherapy system comprising:
a radiotherapy apparatus control device; and
a radiotherapy apparatus,
wherein the radiotherapy apparatus includes:
a radiation source for radiating a radiation; and
a rotating traveling gantry for supporting the radiation source,
wherein the radiotherapy apparatus control device includes:
an imaging part configured to obtain an X-ray image, with reference to imaging timing correction data relating a plurality of gantry angle to a plurality of imaging timing correction amounts, by causing the radiation source to radiate the radiation at a radiating timing calculated on the basis of (i) an imaging timing at which the radiation source supported by the rotating traveling gantry is arranged at a predetermined imaging angle and (ii) an imaging timing correction amount, included in the plurality of imaging timing correction amounts, related to a gantry angle at which the rotating traveling gantry is arranged at the imaging timing;
a reconstruction part configured to calculate three-dimensional data of the X-ray image on the basis of the X-ray image; and
a weighting calculation part configured to calculate a plurality of weightings related to a plurality of X-ray images to be reconstructed as the three-dimensional data on the basis of the X-ray image and the predetermined imaging angle, wherein the radiation source radiates the radiation without rotating more than once during imaging to obtain the X-ray image, wherein the plurality of X-ray images is related to a plurality of imaging angles, wherein the plurality of weightings is calculated so that, when in-unit-angle X-ray images included in the plurality of X-ray images are related to in-unit-angle imaging angles included in a unit angle range, a summation of in-unit-angle weightings related to the in-unit-angle X-ray images is even, the in-unit-angle weighting being included in the plurality of weightings, and wherein the reconstruction part further calculates the three-dimensional data on the basis of the plurality of weightings.

17. The radiotherapy system according to claim 16, wherein the radiotherapy apparatus further includes:

a therapeutic radiation radiating device configured to radiate therapeutic radiation, wherein the therapeutic radiation radiating device is fixed to the rotating traveling gantry.

18. The radiotherapy system according to claim 15, wherein the imaging timing correction data further relates the plurality of gantry angles to a plurality of other imaging timing correction amounts, wherein the radiotherapy apparatus further includes another radiation source for radiating another radiation, wherein the rotating traveling gantry supports the other radiation source, wherein the imaging part (i) calculates another radiating timing on the basis of (a) another imaging timing at which the other radiation source supported by the rotating traveling gantry is arranged at another predetermined imaging angle and (b) another imaging timing correction amount, included in the plurality of other imaging timing correction amounts, related to another gantry angle at which the rotating traveling gantry is arranged at the other another imaging timing, and (ii) obtains another X-ray image by causing the other radiation source to radiate the other radiation at the other radiating timing, and wherein the reconstruction part further calculates the three-dimensional data on the basis of the other X-ray image.

19. The radiotherapy system according to claim 18, wherein the other radiation is radiated in a period when the radiation is not radiated, and wherein the radiation is radiated in a period when the other radiation is not radiated.

20. The radiotherapy system according to claim 19, wherein the predetermined imaging angle and the other predetermined imaging angle are formed so as to coincide with any one of a plurality of imaging angles having equal intervals.

21. The radiotherapy system according to claim 18, wherein the radiotherapy apparatus control device further includes:

an imaging timing correction data creation part configured to create the imaging timing correction data on the basis of a plurality of first absolute angles of then radiation source measured when the rotating traveling gantry is arranged at the plurality of gantry angles and a plurality of second absolute angles of the other radiation source measured when the rotating traveling gantry is arranged at the plurality of gantry angles.

* * * * *